(12) United States Patent
Perlman et al.

(10) Patent No.: US 10,497,474 B2
(45) Date of Patent: Dec. 3, 2019

(54) PATIENT MOVEMENT DETECTION SYSTEM AND METHOD

(71) Applicant: Leaf Healthcare, Inc., Pleasanton, CA (US)

(72) Inventors: David Perlman, Ann Arbor, MI (US); Joseph Himle, Ann Arbor, MI (US)

(73) Assignee: LEAF HEALTHCARE, INC., Pleasanton, CA (US)

( * ) Notice: Subject to any disclaimer, the term of this patent is extended or adjusted under 35 U.S.C. 154(b) by 0 days.

(21) Appl. No.: 15/183,785

(22) Filed: Jun. 16, 2016

(65) Prior Publication Data

US 2017/0049365 A1 Feb. 23, 2017

Related U.S. Application Data

(62) Division of application No. 12/730,663, filed on Mar. 24, 2010, now Pat. No. 10,020,075.

(Continued)

(51) Int. Cl.
*A61B 5/00* (2006.01)
*G16H 40/63* (2018.01)
(Continued)

(52) U.S. Cl.
CPC ............ *G16H 40/63* (2018.01); *A61B 5/1116* (2013.01); *A61B 5/447* (2013.01); *A61B 5/6801* (2013.01); *A61B 5/7275* (2013.01); *A61B 5/742* (2013.01); *A61B 5/746* (2013.01); *G06F 19/00* (2013.01); *G16Z 99/00* (2019.02); *A61B 2560/0443* (2013.01); *A61B 2562/0219* (2013.01); *A61B 2562/18* (2013.01)

(58) Field of Classification Search
CPC .................... A61B 5/447; A61B 5/1115–1117
See application file for complete search history.

(56) References Cited

U.S. PATENT DOCUMENTS

| 5,038,137 A | 8/1991 | Lloyd ........................ 340/573.7 |
| 5,081,447 A * | 1/1992 | Echols ...................... A61F 5/56 |
| | | 200/DIG. 2 |

(Continued)

FOREIGN PATENT DOCUMENTS

| WO | 2007/119070 A1 | 10/2007 | ............. A01K 11/00 |
| WO | 2008/113556 A1 | 9/2008 | ............... A61B 5/11 |

(Continued)

OTHER PUBLICATIONS

U.S. Non-Final Office Action, U.S. Appl. No. 15/187,606, 24 pages, dated Jan. 13, 2017.

(Continued)

*Primary Examiner* — Devin B Henson
*Assistant Examiner* — H. Q. Nguyen
(74) *Attorney, Agent, or Firm* — Slayden Grubert Beard PLLC

(57) ABSTRACT

A monitoring system and method tracks a patient's position over time and ensures that proper turning or other manipulation is done within the time prescribed. Preferably, the techniques herein continuously monitor patient position and alert medical or other personnel of the need for turning or other patient manipulation. The system may be implemented within a medical or other care facility, or within a patient's home.

16 Claims, 7 Drawing Sheets

Related U.S. Application Data

(60) Provisional application No. 61/162,992, filed on Mar. 24, 2009, provisional application No. 61/162,993, filed on Mar. 24, 2009.

(51) Int. Cl.
*A61B 5/11* (2006.01)
*G06F 19/00* (2018.01)
*G16Z 99/00* (2019.01)

(56) References Cited

U.S. PATENT DOCUMENTS

| | | | |
|---|---|---|---|
| 5,146,206 A * | 9/1992 | Callaway | A61B 5/1116 200/DIG. 2 |
| 5,355,892 A | 10/1994 | Saltzstein et al. | 600/523 |
| 5,588,437 A | 12/1996 | Byrne et al. | 600/504 |
| 5,623,760 A | 4/1997 | Newham | 29/622 |
| 5,669,377 A | 9/1997 | Feen | |
| 5,769,784 A | 6/1998 | Barnett et al. | 600/300 |
| 5,941,836 A | 8/1999 | Friedman | 600/595 |
| 6,014,346 A | 1/2000 | Malone | 368/10 |
| 6,030,351 A | 2/2000 | Schmidt et al. | 600/592 |
| 6,129,686 A | 10/2000 | Friedman | 600/595 |
| 6,287,253 B1 | 9/2001 | Ortega et al. | 600/300 |
| 6,447,460 B1 | 9/2002 | Zheng | |
| 6,611,783 B2 * | 8/2003 | Kelly, Jr. | A61B 5/0002 340/573.1 |
| 6,646,556 B1 | 11/2003 | Smith et al. | 340/573.1 |
| 7,017,416 B1 | 3/2006 | Liu et al. | 73/702 |
| 7,030,764 B2 | 4/2006 | Smith et al. | 340/573.1 |
| 7,251,845 B2 | 8/2007 | Schaller et al. | 5/613 |
| 7,325,453 B2 | 2/2008 | Bremer et al. | |
| 7,378,975 B1 | 5/2008 | Smith et al. | 340/573.1 |
| 7,557,718 B2 | 7/2009 | Petrosenko et al. | 340/573.1 |
| 7,634,379 B2 | 12/2009 | Noble | |
| 7,698,830 B2 | 4/2010 | Townsend et al. | 33/512 |
| 7,751,285 B1 | 7/2010 | Cain | 368/82 |
| 7,753,861 B1 | 7/2010 | Kahn et al. | 600/595 |
| 8,085,153 B2 | 12/2011 | O'Connor et al. | 340/573.1 |
| 8,237,551 B2 | 8/2012 | Sweeney | |
| 8,475,368 B2 | 7/2013 | Tran et al. | 600/300 |
| 8,604,916 B2 | 12/2013 | McNeely | |
| 8,674,826 B2 | 3/2014 | Becker et al. | |
| 8,684,900 B2 | 4/2014 | Tran | |
| 8,781,504 B1 | 7/2014 | Liu | |
| 9,005,141 B1 | 4/2015 | Najafi et al. | 600/595 |
| 9,141,974 B2 | 9/2015 | Jones et al. | |
| 2001/0032059 A1 | 10/2001 | Paul, Jr. et al. | 702/150 |
| 2004/0046668 A1 | 3/2004 | Smith et al. | 340/573.7 |
| 2005/0033200 A1 | 2/2005 | Soehren et al. | 600/595 |
| 2005/0049514 A1 | 3/2005 | Iwamiya et al. | 600/503 |
| 2005/0172398 A1 | 8/2005 | Smith et al. | 5/81.1 R |
| 2006/0001545 A1 | 1/2006 | Wolf | 340/573.1 |
| 2006/0089538 A1 | 4/2006 | Cuddihy et al. | 600/300 |
| 2006/0238333 A1 | 10/2006 | Welch et al. | 340/539.2 |
| 2006/0270949 A1 | 11/2006 | Mathie et al. | 600/595 |
| 2006/0279426 A1 | 12/2006 | Bonnet | |
| 2007/0073132 A1 | 3/2007 | Vosch | 600/393 |
| 2007/0093698 A1 | 4/2007 | Goldberger et al. | 600/310 |
| 2007/0118056 A1 | 5/2007 | Wang et al. | 600/595 |
| 2007/0149360 A1 | 6/2007 | Narayanaswami | 482/8 |
| 2007/0159332 A1 | 7/2007 | Koblasz | 340/572.1 |
| 2008/0001735 A1 | 1/2008 | Tran | 340/539.22 |
| 2008/0129518 A1 | 6/2008 | Carlton-foss | 340/573.1 |
| 2008/0262320 A1 | 10/2008 | Schaefer et al. | 600/300 |
| 2008/0272918 A1 | 11/2008 | Ingersoll | |
| 2008/0278336 A1 | 11/2008 | Ortega et al. | 340/573.5 |
| 2009/0024005 A1 | 1/2009 | Lewicke et al. | 600/301 |
| 2009/0024065 A1 | 1/2009 | Einarsson | 602/26 |
| 2009/0069642 A1 | 3/2009 | Gao et al. | 600/300 |
| 2009/0099480 A1 | 4/2009 | Salgo et al. | 600/595 |
| 2009/0112072 A1 | 4/2009 | Banet et al. | 600/301 |
| 2009/0237264 A1 | 9/2009 | Bobey et al. | 340/815.69 |
| 2009/0254003 A1 | 10/2009 | Buckman | |
| 2009/0318908 A1 | 12/2009 | Van Pieterson et al. | 606/9 |
| 2010/0121227 A1 | 5/2010 | Stirling et al. | 600/595 |
| 2010/0156653 A1 * | 6/2010 | Chaudhari | G01C 9/00 340/686.1 |
| 2010/0298742 A1 | 11/2010 | Perlman et al. | 600/595 |
| 2011/0050411 A1 | 3/2011 | Schuman | |
| 2011/0066007 A1 | 3/2011 | Banet et al. | 600/301 |
| 2011/0082672 A1 | 4/2011 | Hardigan | 703/2 |
| 2011/0098615 A1 * | 4/2011 | Whalen | A63B 21/00181 601/151 |
| 2011/0156915 A1 | 6/2011 | Brauers et al. | 340/573.4 |
| 2011/0201972 A1 | 8/2011 | Ten Kate | 600/595 |
| 2011/0263950 A1 | 10/2011 | Larson et al. | 600/301 |
| 2012/0029392 A1 | 2/2012 | Jin et al. | 600/595 |
| 2012/0101770 A1 | 4/2012 | Grabiner et al. | 702/141 |
| 2012/0277637 A1 | 11/2012 | Vahdatpour et al. | 600/595 |
| 2013/0096390 A1 | 4/2013 | Weller-Brophy | |
| 2013/0141233 A1 | 6/2013 | Jacobs | |
| 2014/0188638 A1 | 7/2014 | Jones et al. | 705/16 |
| 2015/0082542 A1 | 3/2015 | Hayes et al. | 5/600 |

FOREIGN PATENT DOCUMENTS

| | | | |
|---|---|---|---|
| WO | 2010/105045 A2 | 9/2010 | A61B 5/02 |
| WO | 2010/111363 A2 | 9/2010 | A61B 5/103 |

OTHER PUBLICATIONS

U.S. Final Office Action, U.S. Appl. No. 12/730,663, 22 pages, dated May 9, 2017.

U.S. Non-Final Office Action, U.S. Appl. No. 12/730,663, 19 pages, dated Jan. 10, 2018.

U.S. Final Office Action, U.S. Appl. No. 15/187,606, 20 pages, dated Aug. 31, 2017.

U.S. Final Office Action, U.S. Appl. No. 15/187,606, 18 pages, dated Aug. 31, 2018.

U.S. Non-Final Office Action, U.S. Appl. No. 15/187,624, 23 pages, dated Jun. 29, 2018.

U.S. Non-Final Office Action, U.S. Appl. No. 15/187,606, 23 pages, dated Apr. 5, 2018.

U.S. Advisory Action, U.S. Appl. No. 15/187,606, 3 pages, dated Oct. 30, 2018.

U.S. Final Office Action, U.S. Appl. No. 15/187,624, 18 pages, dated Jan. 31, 2019.

U.S. Non-Final Office Action, U.S. Appl. No. 15/718,549, 23 pages, dated Feb. 6, 2019.

U.S. Non-Final Office Action, U.S. Appl. No. 16/181,436, 21 pages, dated Feb. 6, 2019.

Wang, Jue et al., "A Compound Sensor for Biomechanical Analyses of Buttock Soft Tissue in Vivo," Journal of Rehabilitation Research and Development, vol. 37, No. 4, pp. 433-443, Dec. 14, 1999.

Lowne, D.R., "Designing a Low-Cost Mattress Sensor for Automated Body Position Classification," IEEE Engineering in Medicine and Biology 27th Annual Conference, pp. 6437-6440, 2005.

DeFloor, Tom et al., "The Effect of Various Combinations of Turning and Pressure Reducing Devices on the Incidence of Pressure Ulcers," International Journal of Nursing Studies, vol. 42, No. 1, pp. 37-46, Jan. 2005.

Wai, A.A. et al., "Sleeping Patterns Obvservation for Bedsores and Bed-Side Falls Prevention," Annual International Conference of the IEEE Engineering in Medicine and Biology Society, pp. 6087-6090, 2009.

Hsia, C.C. et al., "Analysis and Comparison of Sleeping Posture Classification Methods using Pressure Sensitive Bed System," Annual International Conference of the IEEE Engineering in Medicine and Biology Society, pp. 6131-6134, Sep. 2009.

Yip, Marcus et al., "A Flexible Pressure Monitoring System for Pressure Ulcer Prevention," 31st Annual International Conference of the IEEE EMBS, Minneapolis, Minnesota, pp. 1212-1215, Sep. 2, 2009.

* cited by examiner

Numbers in green can be fixed or
adjusted to fit individual patient needs

*Rotation is invalid if patient returns
to P=0± 15° before 30 minutes has lapsed

PATIENT MOVEMENT DETECTION SYSTEM AND METHOD

RELATED APPLICATIONS

This application is based on and claims priority from Ser. No. 61/162,992, filed Mar. 24, 2009, and from Ser. No. 61/162,993, filed Mar. 24, 2009.

BACKGROUND

Patients who suffer from conditions such as epilepsy, asthma, chronic heart disease, Alzheimer's, and other conditions with unpredictable outcomes may need to be constantly monitored for timely assistance and safety. Additionally, patients who suffer from conditions that require periodic shifting of their body orientation in order to prevent digression of the condition or to promote healing from the condition may also need to be constantly monitored to ensure that the proper shifts in their body orientation take place. Examples of conditions that may require periodic shifting may include mobility-limiting conditions such as wheel chair confinement, Restless Leg Syndrome, infants that tend to roll over onto their stomach, or patients at risk for pneumonia that must sit up periodically. Many patients who suffer from such conditions are not monitored continuously because they may live at home by themselves or where family members can not be present at all times or be in a health care facility where attendants are cycled in between patients. As a result, occurrences of life threatening events may go unnoticed until it is too late or shifts in body orientation may be missed, resulting in skin ulcers, pneumonia, suffocation, or any other life-threatening conditions. Currently available patient movement monitoring systems mainly monitor the location of the patient and do not have the capability of detecting small movements such as shifts in body orientation or seizures. Additionally, currently available patient movement monitor systems are typically specialized to monitor for one or two conditions and are not adaptable to multiple conditions that a patient may have concurrently or to multiple patients with different conditions.

A particular problem area concerns pressure ulcers. As patients who suffer from mobility limiting conditions must be monitored and shifted at certain time intervals to minimize the chance for the occurrence of skin ulcers, also known as bed sores. If a patient is left in an orientation for a long time period (e.g., for over 2 hours), there is a risk for development of skin ulcers on one or more contact points along the body. Currently, nurses in health care facilities where such patients are housed visit and "turn" patients at certain time intervals. This method does not, however, take into account movements of the patient in between nurse visits. A common scenario is as follows. In a first visit, a nurse may have assisted a patient to shift from the right towards the left, but in between the first visit and a second visit, the patient may have shifted back towards the right, only to shift back towards the left right before the second visit. From the nurse's perspective, the patient has been on his left for the period between the first and second visits and thus concludes that the patient should now be shifted towards the right, resulting in the patient spending too much time shifted towards the right. In health care facilities, there are commonly too few nurses to continuously monitor any one patient, thus making it nearly impossible to be aware of the shifts that may happen in between any two visits from the nurse.

BRIEF SUMMARY

A monitoring system and method tracks a patient's position over time and ensures that proper turning is done within the time prescribed. Preferably, the techniques herein continuously monitor patient position and alert medical or other personnel of the need for turning or other patient manipulation. The system may be implemented within a medical or other care facility, or within a patient's home.

In one embodiment, a monitoring system comprises several components: a sensor, a monitor, and an output device. The sensor is adapted to be carried by a patient and outputs spatial information associated with the patient's physical orientation. The monitor is in operative communication with the sensor to receive the spatial information together with temporal information. The monitor uses the spatial and temporal information to determine whether the patient is following a patient turn protocol. If not, a notification is provided by the output device so that remedial action can be initiated.

The foregoing has outlined some of the more pertinent features of the invention. These features should be construed to be merely illustrative. Many other beneficial results can be attained by applying the disclosed invention in a different manner or by modifying the invention as will be described.

BRIEF DESCRIPTION OF THE FIGURES

For a more complete understanding of the disclosed invention and the advantages thereof, reference is now made to the following descriptions taken in conjunction with the accompanying drawings, in which.

DESCRIPTION OF REPRESENTATIVE EMBODIMENTS

The following description of several embodiments is not intended to limit the invention, but rather to enable any person skilled in the art to make and use this invention.

Figure 1:
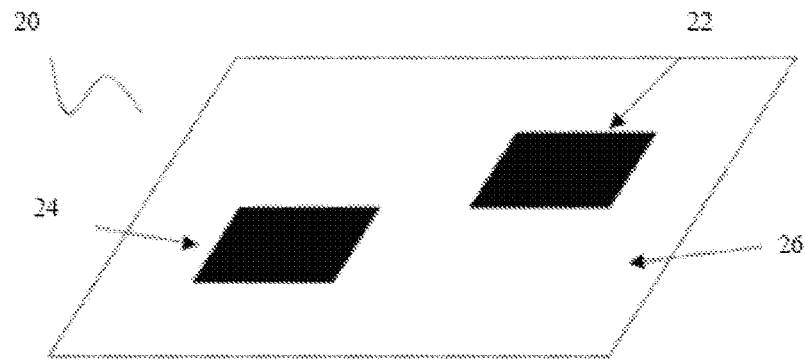
FIG. 1 is a schematic representation of the patient follower in a representative embodiment.
Figure 2:
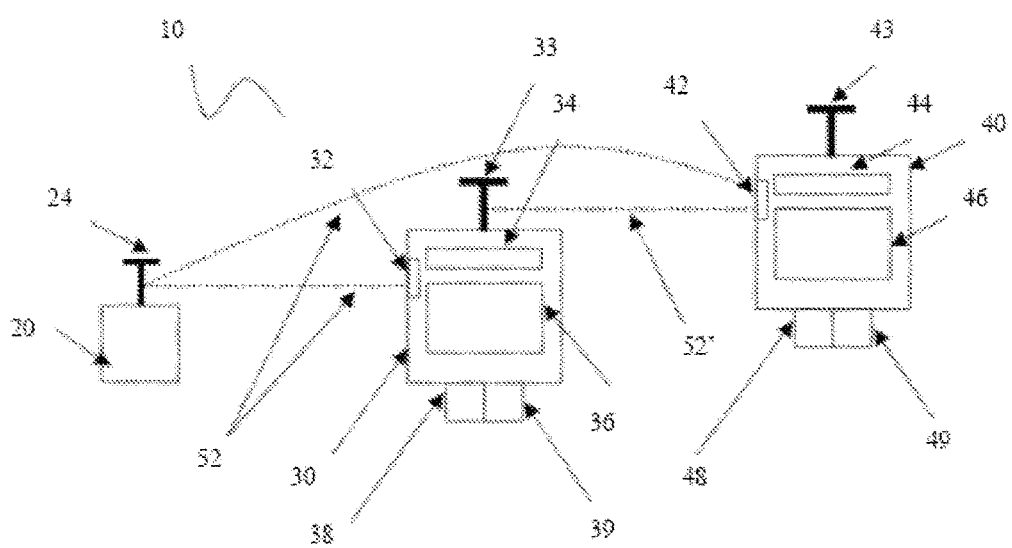
FIG. 2 is a schematic representation of the movement detection system in a representative embodiment.

As shown in FIGS. 1 and 2, an illustrative movement detection system 10 includes a patient follower 20 that includes a sensor 22 that detects movement, a follower transmitter 24 that transmits a signal 52 indicating the occurrence of a movement, and a base 26 that couples the sensor 22 and the follower transmitter 24 to the patient. In one embodiment, the patient follower is a physically wearable, potentially disposable sensor device that monitors the patient's position and transmits the information to one or more other devices. The signal 52 preferably is transmitted to a bedside receiving station 30 and the bedside receiving station 30 then preferably transmits a signal 52' to an attendant (e.g., nurse) receiving station 40. Alternatively, the follower transmitter 24 may transmit the signal 52 directly to the attendant receiving station 40. The bedside receiving station 30 and/or the attendant receiving station 40 preferably functions to interpret the data from the signal 52 to determine the need for attention. Alternatively, the patient follower 20 may function to interpret data from the sensor 22 to determine the need for attention. The method for determining the need for attention may be adjusted for any number of applications, thus allowing the system to be adapted to a variety of applications. The movement detection system 10 also preferably receives and stores data related to the movements detected. However, any other arrangement of the movement detection system 10 suitable to monitoring a patient may be used.

Figure 4:
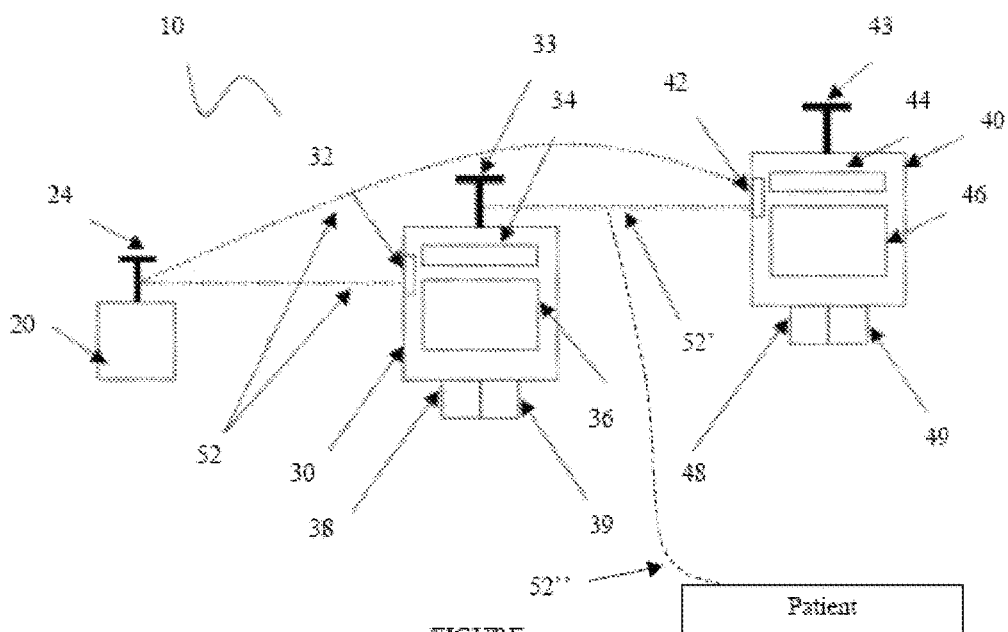
FIG. 4-8 are schematic representations of variations of the movement detection system.

As seen in FIG. 4, the movement detection system may also include a signal 52" that is sent to the patient. The signal preferably provides an indication to the patient, e.g., to shift orientation, which allows the patient the knowledge and opportunity to shift himself or herself.

1. Patient Follower

The patient follower 20 functions to follow the user and continuously monitor the patient for movements that may need to be addressed by an attendant (e.g., an attendant, a family member, a remote communication center). The patient follower 20 is preferably coupled to the patient's body and is preferably wireless (e.g., the device preferably includes a self-contained power source and includes a wireless transmitter) to minimize discomfort to the patient, but may alternatively be wired (for either power or communications). Any other arrangement of the patient follower 20 suitable to continuously monitor the patient for movements may be used.

The sensor 22 functions to sense movement and orientation of the patient. The sensor 22 preferably is coupled to the patient through the base 26 (which, for example, may be a holder affixed to or carried by the patient) and is preferably capable of determining orientation and changes in orientation such that, when coupled to the patient, changes in the sensor's readings will directly indicate changes in the patient's orientation. The sensor 22 is preferably an accelerometer that provides data for any orientation. The accelerator may be a 3-axis accelerometer, but may alternatively be a 2-axis accelerometer with an orientation indicator to indicate the proper orientation of the sensor 22 relative to the patient.

The sensor 22 may alternatively be a sensor that is triggered only when one of plurality of set states is present, each state correlating to a specific orientation of the patient, for example, the patient lying down, sitting, standing, or walking. In this variation of the sensor 22, the sensor 22 selectively reports data regarding the orientation of the patient, simplifying both the communication and the interpretation of the data from the sensor 22. The sensor 22 in this variation may an optical sensor that monitors fluid within a straight or curved tube wherein the fluid shifts within the tube as the patient shifts, a contact switch that monitors a ball bearing within a straight or curved tube wherein the ball within the tube shifts as the patient shifts, or any suitable type of tilt sensor or vibration sensor. However, the sensor 22 may be any other sensor suitable to indicate orientation and/or movement.

In an iPhone®-based application such as described below, the sensor itself may be implemented as an application on the device itself, it which case the native accelerometer in the device can be used for the above-described purposes of determining patient orientation.

The follower transmitter 24 functions to transmit a signal 52 from the patient follower 20 that indicates the patient's orientation and/or the occurrence of a movement that may require the attention of an attendant. The follower transmitter 24 is preferably a conventional signal transmitter, but may alternatively be any suitable device that transmits a signal. The follower transmitter 24 preferably transmits the signal 52 through a wireless network such as WiFi, cellular, Bluetooth, ZigBee, Internet Protocol (IP)-based network, or any other suitable network, further allowing the patient follower 20 to be a wireless component. Alternatively, the follower transmitter 24 may transmit the signal 52 through Ethernet, cable, or any other suitable wired network.

The sensor 22 and the follower transmitter 24 are preferably in communication with each other. The follower transmitter 24 preferably remains in a stand-by mode until data is received from the sensor 22, but may alternatively actively retrieve data from the sensor 22 to be transmitted through the signal 52. In both variations, the follower transmitter 24 preferably receives data from the sensor 22 and transmits the signal 52 at regular intervals, but the follower transmitter 24 may alternatively continuously receive data from the sensor 22 while transmitting the signal 52 at regular intervals. Alternatively, the follower transmitter 24 may receive data from the sensor 22 only when a movement that may require attention is detected. However, any other suitable timing or arrangement of receiving and sending data between the sensor 22, the follower transmitter 24, and the signal 52 may be used.

The base 26 functions to couple the sensor 22 and the follower transmitter 24 to the patient. The base 26 preferably includes at least one portion of a type of adhesive that may be coupled to the patient's skin for a period of time and removed when finished. The base 26 may also include a second portion of a second type of adhesive appropriate to couple the sensor 22 and the follower transmitter 24 to the base 26. The sensor 22 and the follower transmitter 24 is preferably pre-coupled to the base 26 to facilitate coupling of the patient follower 10 to the patient, but may alternatively be surgical tape, medical tape, or any other suitable adhesive to secure the sensor 22 and the follower 24 to the patient. The base 26 is preferably disposable, but may alternatively be reusable. The base 26 may also include rigid portions to protect the sensor 22 and the follower transmitter 24. The rigid portions may be separately molded to contain the sensor 22 and the follower transmitter 24 and then coupled to the base 26. The base 26 may also include channels for data transfer and/or power transfer, for example, a printed circuit. The base 26 is preferably of a material that is water and sweat-resistant to both protect the sensor 22 and the follower transmitter 24 and to remain robust under conditions commonly seen by the patient. However, any other suitable material and arrangement of the base 26 may be used.

Figure 3:
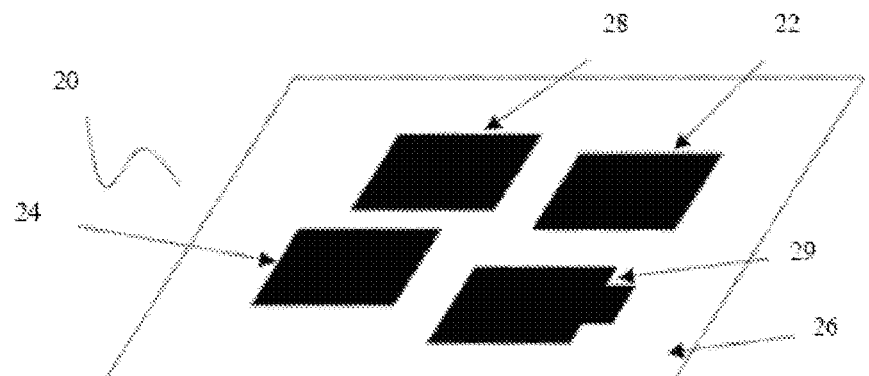
FIG. 3 is a schematic representation of a variation of the patient follower of a representative embodiment.

The patient follower 20 may also includes a power source 28, as shown in FIG. 3. The power source 28 is preferably coupled to the sensor 22 and/or the follower transmitter 26, but may alternatively be coupled to the base 26. The power source 28 is preferably one of several variations. In a first variation, the power source 28 is a battery. The battery is preferably a small, flat battery such as a coin (or button) cell (e.g., lithium-based) battery, but may alternatively be any suitable battery. In a second variation, the power source 28 is preferably a power cord that attaches to the power grid. Although the power source 28 is preferably one of these two variations, the power source 28 may be any suitable device to supply power to the elements coupled to the patient follower 20. In an RFID variation, the device may be powered by a transmitter signal received at the device.

The patient follower 20 may further include a follower storage device 29, as shown in FIG. 3, coupled to the sensor 22 and/or the follower transmitter 24. The follower storage device 29 of an illustrative embodiment functions to store information related to the patient follower 20 and/or any movement detected by the sensor 22. The follower storage device 29 is preferably a conventional memory chip, such as RAM, a hard drive, or a flash drive, but may alternatively be any suitable device able to store information. The information that the follower storage device 29 may store includes the patient's orientation, the duration of the patient's current orientation, the current time, an indication of a necessary change in orientation, the patient's change in orientation, the magnitude of the change in orientation, the frequency the number of orientation changes that have occurred, the frequency of orientation changes, the date and time of any given orientation change, the date and time of an attendant's response to any given orientation change, the average response time of an attendant, the patient identification number, the patient's personal information, the patient's health information, the patient's attendant's and/or attendant's information, and/or any other suitable information.

2. The Signal

The signal 52 is transmitted (preferably over the air) by the follower transmitter 24 and includes data representative of the orientation and/or movement of the patient. The signal 52 may include any or all of the following information: the patient's orientation, the duration of the patient's current orientation, the current time, an indication of a necessary change in orientation, the patient's change in orientation, the magnitude of the change in orientation, the number of orientation changes that have occurred, the frequency of orientation changes, the date and time of any given orientation change, the date and time of an attendant's response to any given orientation change, the average response time of an attendant, the patient identification number, the patient's personal information, the patient's health information, the patient's attendant's and/or attendant's information, and/or any other suitable information. The signal 52 is preferably one of several variations.

In a first variation, the signal 52 is transmitted by the follower transmitter 24 to the bedside receiving station 30 and/or the attendant receiving station 40, as shown in FIG. 2, to be interpreted. The bedside receiving station 30 and/or the attendant receiving station 40 then uses the data within the signal 52 to determine the need for attention (e.g., the need for a nurse to turn the patient and, if a need is determined, to warn the attendant of the patient's need for attention, to indicate the turn of the patient, and/or to indicate the position that would be most appropriate for the patient at the current time.

In a second variation, the signal 52 is transmitted to the bedside receiving station 30 and/or the attendant receiving station 40 when the patient follower 20 detects a need for attention. In this variation, the bedside receiving station 30 and/or the attendant receiving station 40 functions to warn the attendants of the patient's need for attention e.g., the need for a nurse to turn the patient and, if a need is determined, to warn the attendant of the patient's need for attention, to indicate the turn of the patient, and/or to indicate the position that would be most appropriate for the patient at the current time.

In a third variation, the patient follower 20 functions to transmit the signal 52 at regular intervals to the bedside receiving station 30 and/or the attendant receiving station 40. In this variation, the bedside receiving station 30 and/or the attendant receiving station 40 function to display the data from the signal 52 for an attendant to interpret. The receiving stations 30 and/or 40 preferably also function to interpret the signal 52 to display indications or warnings to further engage the attendant's attention when the patient needs attention (e.g., when the patient needs to be turned to a different position).

In a fourth variation, the patient follower 20 functions as a first level warning or indication of a potential patient need for attention that is further verified by the bedside receiving station 30 and/or the attendant receiving station 40. In this variation, the patient follower 20 functions to transmit the signal 52 when a movement of a certain degree is detected. Upon receiving the signal 52, the receiving stations 30 and/or 40 interpret the movement relative to previously stored movements to determine whether there is a real need for attention. For example, a patient on a wheel chair may have been shifted to the left for a duration of time, and slightly before the patient is due to be shifted to the right by an attendant, the patient shifts to the right without assistance. The patient follower 20 will send a signal indicating the shift and the potential need for attention, but the receiving stations 30 and/or 40 may evaluate this with the historical data to determine that there is no need for attention because the attendant is scheduled to shift the patient towards the right in a relatively short time and will instead indicate that the routine shifting of the patient has already been carried out, saving the attendant an extra visit.

In any of the above variations, upon detection of the need for attendant attention, a signal 52" may be transmitted from the patient follower 20, bedside receiving station 30, and/or attendant receiving station 40 to the patient, as shown in FIG. 4. The signal 52" preferably provides a signaling sensation to the patient and indicates the need for a routine shift in orientation, a warning for having walked too far/ and/or fast, a warning for a non-recommended activity, and/or a warning for any other suitable event. This provides the patient with the knowledge and the opportunity to correct and/or adjust him or herself without the attendant's assistance. By allowing the patient this knowledge and opportunity, a patient that has enough mobility to correct and/or adjust is encouraged to do so, saving the attendant from an unnecessary trip and allowing the attendant to tend other patients with greater need. In this version, the movement detection system 10 preferably functions to monitor the time from when the patient was first notified of the need correct/and or adjust and when the patient carries out the correction and/or adjustment. This data may be useful in determining the willingness of the patient to comply with the notification system. The movement detection system 10 may also detect if the patient has not carried out the correction and/or adjustment after a certain period of time after the notification was sent and preferably sends a warning to the attendant if the patient has not shifted orientation within the period of time. This may indicate the need for attendant attention. Alternatively, if the patient has not corrected and/or adjusted within the period of time, the signal 52" may be resent for a certain number of times before an attendant is notified. The signal 52" is preferably an audible signal such as a beep, an alarm, or a voice. The signal 52" may alternatively be a visual sensation, a tactile sensation and/or any other suitable notification.

Although the signal 52 is preferably at least one of the above variations, the signal 52 may be any suitable signal, including any suitable information, and in any suitable arrangement to represent data on the orientation and/or of the patient. The signal 52 may also be any suitable combination of the above variations.

3. Bedside Receiving Station

Figure 7:
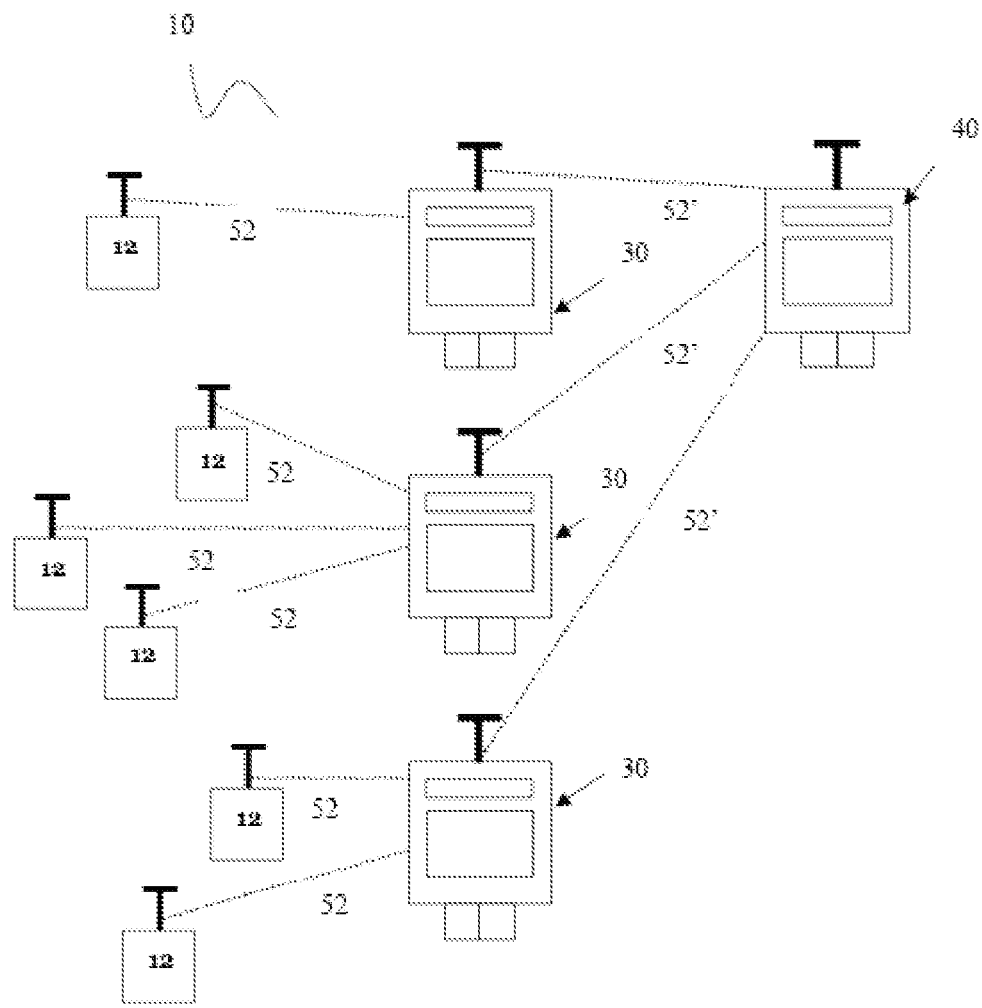

The bedside receiving station 30 functions to receive the signal 52 from the follower transmitter 24 and to receive a signal from the attendant receiving station 40. Additionally, the bedside receiving station 30 may function to receive signals from multiple follower transmitters 24, as there may be multiple regions on the patient wherein movement is monitored, or multiple patients with patient followers 20 in the room, as shown in FIG. 7.

The bedside receiving station preferably includes a bedside receiver 32. The bedside receiver 32 is preferably a conventional signal receiver, but may alternatively be any suitable device to receive a signal. The bedside receiving station 30 is preferably one of several variations.

In a first variation, as shown in FIG. 2, the bedside receiving station 30 is a physical station. The bedside receiving station 30 is preferably located in the patient's room and near the patient's beside. The bedside receiving station 30 may be located near the bedside or coupled to the bed frame. The bedside receiving station 30 may alternatively be located in any suitable location, such as coupled to a patient's stretcher or wheel chair that moves with the patient, such that it can receive the signal 52 from the follower transmitter 24 and receive a signal from the attendant receiving station 40.

Figure 5:
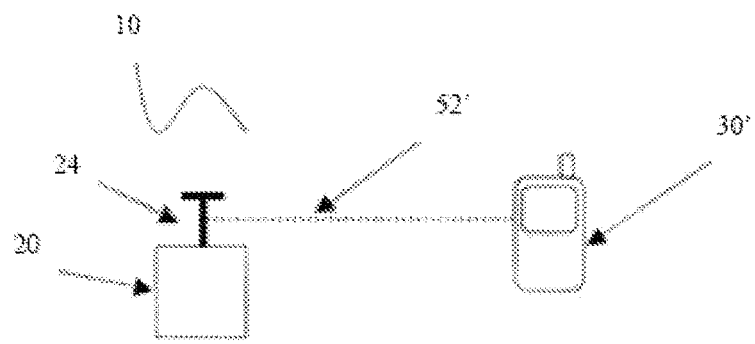

In a second variation, as shown in FIG. 5, the bedside receiving station 30' is a mobile device. The mobile device is preferably a pager to be worn by the attendant or attendant, but may alternatively be a cell phone, a PDA, a smart phone, a laptop computer, or any combination thereof.

In a third variation, the bedside receiving station 30 is coupled directly to the patient follower 20. Although the bedside receiving station 30 is preferably at least one of these three variations, the bedside receiving station 30 may be any suitable device to receive the signal 52 from the follower transmitter 24 and receive a signal from the attendant receiving station 40.

The bedside receiving station 30 may further include a bedside display device 34, as shown in FIG. 2, which functions to display information relevant to the patient follower 20, the patient, and/or the movement detected by the patient follower 20. The bedside display device 34 is preferably a conventional screen such as an LCD screen, a computer monitor, or a television screen. The bedside display device 34 could alternatively be any suitable display device such as Internet webpage. Additionally, the bedside display device 34 may include speakers or alarms such that information may be displayed in an audible fashion as well. The information displayed by the bedside display device 34 may include any or all of the following information: the patient's orientation, the correct orientation for the patient, the duration of the patient's current orientation, the current time, an indication of a necessary change in orientation, the patient's change in orientation, the magnitude of the change in orientation, the number of orientation changes that have occurred, the frequency of orientation changes, the date and time of any given orientation change, the date and time of an attendant's response to any given orientation change, the average response time of an attendant, the patient identification number, the patient's personal information, the patient's health information, the patient's attendant's and/or attendant's information, and/or any other suitable information.

The bedside receiving station 30 may further include a bedside user interface 36, as shown in FIG. 2, which functions to accept an input from a user, such as an attendant or attendant. The bedside user interface 36 is preferably a conventional user interface including buttons, dials, a keyboard, a touch screen, a mouse, a switch, a microphone, and/or any other suitable user interaction device. The information entered by an attendant or attendant into the bedside user interface 36 may include any or all of the following information: the patient's orientation, the correct orientation for the patient, a confirmation for the detected orientation and the actual orientation of the patient, the duration of the patient's current orientation, the current time, an indication of a necessary change in orientation, the patient's change in orientation, the magnitude of the change in orientation, the number of orientation changes that have occurred, the frequency of orientation changes, the date and time of any given orientation change, the date and time of an attendant's response to any given orientation change, the average response time of an attendant, the patient identification number, the patient's personal information, the patient's health information, the patient's attendant's and/or attendant's information, and/or any other suitable information. While the bedside receiving station preferably includes a user interface with an input, other versions of the motion detection system may omit this feature and/or step.

The bedside receiving station 30 may further include a bedside transmitter 33, as shown in FIG. 2. The bedside transmitter 33 of the preferred embodiments functions to transmit a signal 52' indicating the occurrence of a movement. The bedside transmitter 33 is preferably a conventional signal transmitter, but may alternatively be any suitable device that transmits a signal. The bedside transmitter 33 preferably transmits the signal 52' through a wireless network such as WiFi, cellular, Bluetooth, ZigBee, IP-based network, or any other suitable network. Alternatively, the bedside transmitter 33 may transmit the signal 52' through Ethernet, cable, or any other suitable wired network.

The signal 52' preferably is the same as the signal 52 of the preferred embodiments, but may alternatively be altered by the bedside receiver 30. The bedside receiver 30 may serve as a filter or an interpreter of the signal 52 from the patient follower 20 and only send the signal 52' when attention is required. The signal 52' is preferably transmitted by the bedside transmitter 33.

The bedside receiving station 30 may further include a bedside processor 38 and a bedside storage device 39 coupled to the bedside processor 38, as shown in FIG. 2. The bedside processor 38 is coupled to the bedside receiver 32, the bedside display device 34, the bedside user interface 36, and the bedside transmitter 33. The bedside processor 38 functions to process the information received by the bedside receiver 32 and the bedside user interface 36 and to transmit the relevant information to the bedside display device 34, the bedside transmitter 33, and the bedside storage device 39. The bedside processor 38 is preferably a conventional processor, but may alternatively be any suitable device to perform the desired functions. The bedside storage device 39 of the preferred embodiments functions to store information transmitted by the bedside processor 38, related to the patient follower 20, movements detected by the patient follower 20, and/or the attendant's response to a movement. The bedside storage device 39 is preferably a conventional memory chip, such as RAM, a hard drive, or a flash drive, but may alternatively be any suitable device able to store information.

4. Attendant Receiving Station

The attendant (or "nurse") receiving station 40 of the preferred embodiments functions to receive the signal 52' from the bedside transmitter 33 and may also receive a signal 52 from the follower transmitter 24. Additionally, the attendant receiving station 40 may function to receive signals from multiple bedside transmitters 33, as there may be multiple bedside transmitters 33 in a room or building, as shown in FIG. 7. The attendant receiving station preferably includes an attendant station receiver 42. The attendant station receiver 42 is preferably a conventional signal receiver, but may alternatively be any suitable device to receive a signal. The attendant receiving station 40 is preferably one of several variations.

In a first variation, as shown in FIG. 2, the attendant receiving station 40 is a physical station. The attendant receiving station 40 is preferably located at the nursing or attendant's station or in the hallway. The attendant receiving station 40 may alternatively be located in any suitable location, such as coupled to a patient's stretcher or wheel chair that moves with the patient, such that it can receive the signal 52' from bedside transmitter 33 and may also receive a signal 52 from the follower transmitter 24. The attendant receiving station 40 may also be in a remote location such as a control center.

Figure 6:
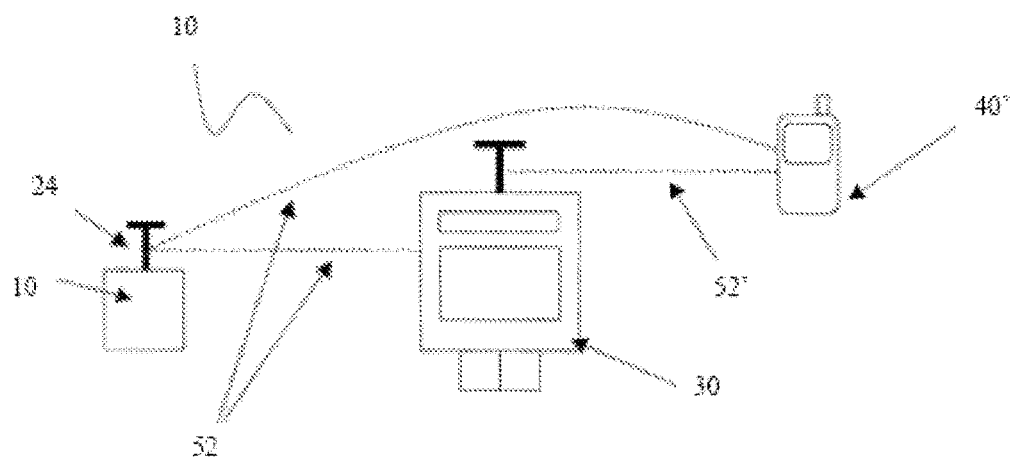

In a second variation, as shown in FIG. 6, the attendant receiving station 40' is a mobile device. The mobile device is preferably a pager to be worn by the attendant or attendant, but may alternatively be a cell phone, a PDA, a smart phone, a laptop computer, or any combination thereof.

In a third variation, the attendant receiving station 40 may be a physical station that includes a mobile device or a series of mobile devices, as described above, that may be worn or held by an attendant or attendant.

In a fourth variation, the attendant receiving station may be a conventional attendant station. In this variation, the movement detection system 10, including the bedside receiving station 30, would interface with the conventional attendant station. The movement detection system 10 would interface with the nursing station through an application programming interface (API) and/or a wireless network such as WiFi, cellular, Bluetooth, ZigBee, Internet-protocol based network, or any other suitable network. Alternatively, the movement detection system 10 would interface with the nursing station through Ethernet, cable, any other suitable wired network, or any combination thereof. Although the attendant receiving station 40 is preferably at least one of these variations, the attendant receiving station 40 may be any suitable device to receive the signal 52' from the bedside transmitter 33 and may also receive a signal 52 from the follower transmitter 24.

The attendant receiving station 40 may further include an attendant station display device 44, as shown in FIG. 2, which functions to display information relevant to the bedside receiving station 30, the patient follower 20, the patient, and/or movement detected by the patient follower 20. The attendant station display device 44 is preferably a conventional screen such as an LCD screen, a computer monitor, or a television screen. The attendant station display device 44 could alternatively be any suitable display device such as Internet webpage. Additionally, the attendant station display device 44 may include speakers or alarms such that information may be displayed in an audible fashion as well. The information displayed by the attendant station display device 44 may include any or all of the following information: the patient's orientation, the correct orientation for the patient, the duration of the patient's current orientation, the current time, an indication of a necessary change in orientation, the patient's change in orientation, the magnitude of the change in orientation, the number of orientation changes that have occurred, the frequency of orientation changes, the date and time of any given orientation change, the date and time of an attendant's response to any given orientation change, the average response time of an attendant, the patient identification number, the patient's personal information, the patient's health information, the patient's attendant's and/or attendant's information, and/or any other suitable information.

The attendant receiving station 40 may further include an attendant station user interface 46, as shown in FIG. 2, which functions to accept an input from a user, such as an attendant or attendant. The attendant station user interface 46 is preferably a conventional user interface including buttons, dials, a keyboard, a touch screen, a mouse, a switch, a microphone, and/or any other suitable user interaction device. The information entered by an attendant or attendant into the attendant station user interface 46 may include any or all of the following information: the patient's orientation, the correct orientation for the patient, confirmation for the detected orientation and the actual orientation of the patient, the duration of the patient's current orientation, the current time, an indication of a necessary change in orientation, the patient's change in orientation, the magnitude of the change in orientation, the number of orientation changes that have occurred, the frequency of orientation changes, the date and time of any given orientation change, the date and time of an attendant's response to any given orientation change, the average response time of an attendant, the patient identification number, the patient's personal information, the patient's health information, the patient's attendant's and/or attendant's information, and/or any other suitable information.

The attendant receiving station 40 may further include an attendant station transmitter 43, as shown in FIG. 2. The attendant station transmitter 43 of the preferred embodiments functions to transmit a signal 52''' indicating an attendant's response to a movement and/or indicating the occurrence of a movement. The attendant station transmitter 43 is preferably a conventional signal transmitter, but may alternatively be any suitable device that transmits a signal. The attendant station transmitter 43 preferably transmits the signal through a wireless network such as WiFi, cellular, Bluetooth, ZigBee, IP-based network, or any other suitable network. Alternatively, the attendant station transmitter 43 may transmit the signal through Ethernet, cable, or any other suitable wired network.

Figure 8:
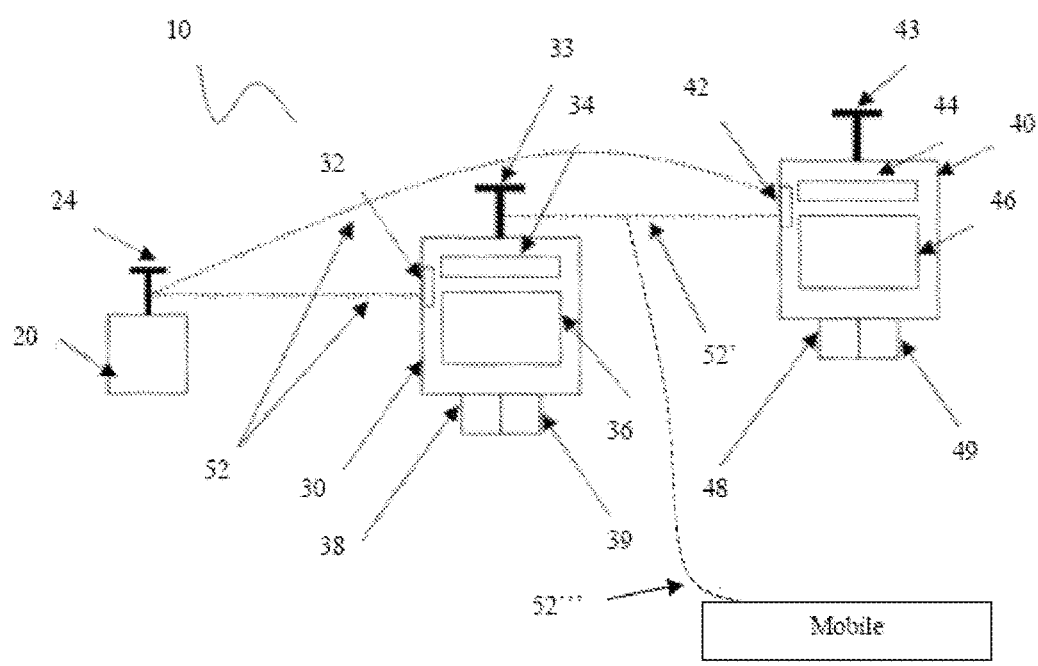

The signal 52''' is transmitted by the attendant station transmitter 43 and indicates an attendant's response to a movement and/or an occurrence of a movement. In the third variation of the attendant receiving station 40, wherein the attendant receiving station is a physical station that includes a mobile device or a series of mobile devices that may be worn or held by an attendant or attendant, the signal 52''' may be sent from the physical station to the mobile device or to the bedside receiving station 30 as shown in FIG. 8. The signal 52''' is preferably one of several variations. In a first variation, the signal indicates an attendant's response to a movement and is transmitted by the attendant station transmitter 43 to the bedside receiving station 30. The signal may include any or all of the following information: the patient's orientation, the duration of the patient's current orientation, the current time, an indication of a necessary change in orientation, the patient's change in orientation, the magnitude of the change in orientation, the number of orientation changes that have occurred, the frequency of orientation changes, the date and time of any given orientation change, the date and time of an attendant's response to any given orientation change, the average response time of an attendant, the patient identification number, the patient's personal information, the patient's health information, the patient's attendant's and/or attendant's information, and/or any other suitable information. In a second variation, the signal indicates the need for attention and is transmitted by the attendant station transmitter 43 to the attendant. The signal 52''' in this variation provides a signaling sensation to the attendant. The signal is preferably an audible signal such as a beep, an alarm, or a voice. The signal may alternatively be a visual sensation and/or a tactile sensation. Although the signal is preferably at least one of these two variations, the signal may be any suitable signal, including any suitable information, to indicate the occurrence of a movement and/or an attendant's response to a movement.

The attendant receiving station 40 may further include an attendant station processor 48 and an attendant station storage device 49 coupled to the attendant station processor 48, as shown in FIG. 2. The attendant station processor 48 is coupled to the attendant station receiver 42, the attendant station display device 44, the attendant station user interface 46, and the attendant station transmitter 43. The attendant station processor 48 functions to process the information received by the attendant station receiver 42 and the attendant station user interface 46 and to transmit the relevant information to the attendant station display device 44, the attendant station transmitter 43, and the attendant station storage device 49. Additionally, the attendant station processor 48 may prioritize the information received by the attendant station receiver 42 and the attendant station user interface 46 (e.g., based on the patient information associated with the given movement) and transmit the prioritized relevant information to the attendant station display device 44, the attendant station transmitter 43, and the attendant station storage device 49. The attendant station processor 48 is preferably a conventional processor, but may alternatively be any suitable device to perform the desired functions. The attendant station storage device 49 of the preferred embodiments functions to store information transmitted by the attendant station processor 48, related to the patient follower 20, the movement detected by the patient follower 20, and/or the attendant's response to a movement. The attendant station storage device 49 is preferably a conventional memory chip, such as RAM, a hard drive, or a flash drive, but may alternatively be any suitable device able to store information.

Alternatively, the attendant receiving station 40 may include an indicator and an attendant station receiver 42, wherein the attendant station receiver 42 functions to receive signal 52 from the patient follower 20 and/or the signal 52' from the bedside receiving station 30, and wherein the indicator is preferably located on the door of the patient's room, but may alternatively be located by the patient's bed, and/or on an indicator panel that is visible to an attendant. The indicator of this variation of the attendant receiving station 40 is preferably a light (e.g. an LED), but may alternatively be an audible alert, a flag, or any other suitable indicator that is visible to the attendant. This variation of the attendant receiving station 40 allows for a relatively inexpensive and simple implementation of the movement detection system 10 in health care facilities and/or a home.

Additionally, because of the lower power usage of this variation of the attendant receiving station 40, the attendant receiving station 40 may be powered using a solar cell that collects power from hallway lights or any other available light source, but may alternatively be powered by a battery. An attendant receiving station 40 of this variation that is mounted to a door may also be powered using the rotational motion of the door as it is opened or closed and/or the rotational motion of a door knob/handle. However, any other suitable power source may be used. In an exemplar usage scenario, an indicator light that is visible to the attendant lights up whenever the movement detection system 10 indicates the need for attendant attention. The indicator light is preferably assigned to a particular patient, allowing the attendant to go to the patient. The attendant may then receive data regarding the action required for the patient from the bedside receiving station 30, a paper chart, and/or any other data containing medium, and determine the correct action to be taken with the patient. The indicator light may be located on the door of the patient's room that is visible to an attendant as the attendant walks by, either as the attendant is making rounds checking on patients or passing by on the way to another task. The indicator light may also be located on an indicator panel by an attendant's station, wherein the indicator panel may include a plurality of indicator lights, each pertaining to a particular patient.

Although the attendant receiving station 40 preferably includes the components described above and is preferably of one of the variations described above, the attendant receiving station 40 may alternatively be of any other suitable arrangement or type.

5. Method to Determine the Need for Attendant Attention

The movement detection system 10 is preferably applicable to a plurality of applications. The method for determining whether the attention of an attendant is necessary is different for each application. However, each method includes the steps of (a) either detecting a shift in the orientation of the patient or detecting the actual orientation of the patent, (b) determining the appropriate orientation of the patient, and (c) sensing elapsed time. The method to evaluate the detected information is preferably one of several variations for a variety of applications.

In a first variation, the movement detection system 10 is preferably used for monitoring required shifts in the patient's orientation to minimize the risk of skin ulcers. In this variation, the patient follower 20 is placed on different portions of the patient's body depending on the type of shift that the movement detection system 10 is detecting. For example, in the case of minimizing the risk of skin ulcers and preventing pneumonia, a patient must be placed in a sitting position periodically after laying down for period of time. In this case, a patient follower 20 may be placed on the patient's torso. Alternatively, two patient followers 20 may be used, a first placed on the patient's torso and a second placed on the patient's hip where relative data between the first and second patient followers 20 is analyzed to determine whether the patient is sitting or lying down. In a second example, in the case where a patient is confined to a wheelchair, the risk of skin ulcers is minimized by periodic shifts in the patient's weight within the wheelchair. In this case, a patient follower 20 may be placed on the patient's hip to detect whether the patient's position has changed within a period of time, indicating a shift in weight. In a third example, the patient may be an infant wherein a resting position on the infant's stomach is undesired. In this case, the patient follower 20 may be placed anywhere along the infant's abdomen, chest, and/or back area to detect if the infant has shifted onto its stomach. In a fourth example, the patient may be suffering from RLS (Restless Leg Syndrome) wherein the leg is preferably shifted after certain periods of time.

In this first variation, the maximum period of time that the patient may be in a certain orientation may be manually inputted into the movement detection system 10 by an attendant. The system 10 then preferably utilizes the maximum time inputted by the attendant as a time-on threshold and detects the time the patient has been in any one position and compares the time detected to the time-on threshold. If the time detected is greater than the time-on threshold, then warning is sent to the attendant and/or the patient to notify the need for a shift in orientation. The attendant may alternatively input a minimum period of time that the patient should be in a first orientation, wherein the system 10 utilizes the minimum period of time as a minimum time-on threshold. The system 10 detects the time the patient has been in the first orientation and compares the time detected to the minimum time-on threshold and when the patient shifts to a second orientation when the time detected is less than the minimum time-on threshold, then a warning is sent to the attendant and/or the patient to notify the need to return to the first orientation.

In a second variation, the movement detection system 10 is preferably used for the detection of occurrences of sudden convulsive attacks with relatively high frequency such as asthma, seizures, heart attacks, and/or excessive sneezing. In this variation, the patient follower 20 may be placed along the torso area of the chest or any other location on the body of the patient wherein the convulsions are most prominent. For example, in the case of an asthma attack, there may be a higher degree of movement in the torso region of the patient, whereas in the case of seizures, there may be a higher degree of movement by the head area of the patient. In this variation, the movement detection system 10 looks for a frequency of movement that matches a frequency seen in the type of attack that the system 10 is monitoring for. This frequency for each type of convulsion may be preprogrammed into the movement detection system 10 and then selected by an attendant based upon convulsion type. The frequency may also be inputted directly into the system by the attendant based upon the unique characteristics of each patient, for example, some patients may be prone to lower frequency convulsions while others may be prone to higher frequency convulsions. The frequency may also be a variable frequency to match the type of condition that is being monitored. For example, some conditions may result in an erratic frequency, while others may be defined by a series of frequencies or an increase and/or decrease of frequency. However, any suitable series or set of frequencies may be used.

In a third variation, the movement detection system 10 is preferably used for the detection of walking, excessive motion, moving onto one side (such as moving onto a side with an injury or moving onto their stomach position and possibly involving a Sudden Infant Death Syndrome situation), lack of minute (such as lack of breathing), or moving away from a lying down position when the patient should be confined to the bed. In this variation, the patient follower 20 may be coupled to any portion of the patient's body that best indicates the motion that is being monitored. For example, if walking activities are to be monitored, the patient follower 20 may be coupled to the patient's leg and if the action of getting up from a bed is to be monitored, then the patient follower 20 may be coupled to the patient's chest. In this variation, the degree of movement may be used to trigger the occurrence of an undesirable event (e.g., getting up from the bed, or falling down). A pattern may also be detected for the motion of walking and the number of steps taken by the patient may be detected to determine if there is excessive movement or the patient has moved too far. The pace of walking may also be monitored to determine of the patient is walking too fast, which may result in strenuous activity. Similar to other variations, the thresholds for each of the conditions may be inputted by an attendant to accommodate to each unique patient.

Although the method for determining the need for attendant attention is preferably at least one of the above variations, the method may be of any suitable type or sequence. The method for determining the need for attendant attention may also be any suitable combination of the above variations. Several methods may also be used concurrently to accommodate to patients with multiple needs.

When the system is used to prevent pressure ulcers, the method further includes interpreting whether data from the sensor indicates a shift in orientation of the patient. The step of determining the appropriate orientation of the patient preferably is one of several variations.

In a first variation, the step of determining the appropriate orientation of the patient uses a proportional relationship between a time-on value and a time-off value. The time-on value is a measured value indicating the time the patient has been in a first orientation and the time-off value is a resultant value that is calculated based upon the time-on value, wherein the time-off value indicates the minimum length of time the patient should be shifted away from the first orientation after the patient has been in the first orientation for the time-on value to lower the risk of a skin ulcer.

The step of determining the appropriate orientation of the patient may further use a constant (user-selected, system-selected, or the like) that is an indicator of health, hereafter known as the health indicator constant. The health indicator constant is preferably a value that is derived from the patient's age, circulatory health, medication, diseases, and any other ailments that the patient may have. The health indicator constant may alternatively include any other factors that may contribute to the patient's overall health. For example, the health indicator constant for a patient with poor circulatory health may be higher than the health indicator constant for a patient with relatively better circulatory health, resulting in a longer time-off value for the patient with poor circulatory health relative to the time-off value for the patient with relatively better circulatory health, allowing damaged skin of the patient with poor circulatory health to have more time to recover from extended pressure applied from the patient's orientation. This proportional relationship between the time-off value and the time-on value with a health indicator constant allows for the movement detection system 10 to more effectively accommodate to individual patients and to more efficiently use the precious time of the nurses. The health indicator constant is preferably calculated based upon the patient's statistics, but may alternatively be manually entered by a medical practitioner. Manual input from a medical practitioner allows the system to further accommodate to the unique statistics of each patient by utilizing the opinion of a medical practitioner directly familiar with the patient. The manual input for the health indicator constant may be from a scale indicating relative health of the patient, for example, a scale from 1 to 5 with 5 being very healthy and 1 being not healthy, but may alternatively be a matrix of information that is entered by the medical practitioner, wherein the information is to be interpreted by the motion detection system 10 to determine the appropriate health indicator constant. In this variation, the determined appropriate health indicator constant is preferably adjustable by the medical practitioner to further accommodate to the patient's individual needs. While the manual input for the health indicator may be optimal, the motion detection system 10 of other variations may omit this particular feature and/or step.

In an exemplary use of the first variation, the motion detection system 10 preferably detects the time the patient is in a first orientation to determine a time-on value while determining the respective time-off value for the first orientation. If the patient is shifted to a second orientation, either by a nurse or by him or herself, the time the patient is in the second orientation is detected and compared to the calculated time-off value. If the patient is shifted back towards the first orientation at a time less than the calculated time-off value, then a warning or indication is issued to the nurse that attention is necessary. The motion detection system 10 also preferably detects when a patient has been in the first orientation for too long, for example, for over 2 hours, and issues a warning to the nurse that attention is necessary.

In a second variation, the step of determining the appropriate orientation of the patient uses a time-on threshold and a time-off threshold to be compared to a time-on value and a time-off value. The time-on value is a measured value indicating the length of time the patient has been in a first orientation and the time-off value is a measured value indicating the length of time the patient is not in a first orientation. The time-on threshold indicates the maximum time the patient is safely in a first orientation and the time-off threshold indicates the minimum time the patient should be in an orientation other than the first orientation before safely resuming the first orientation. The motion detection system 10 preferably compares the time-on value to the time-on threshold until an event such as the time-on value being above the time-on threshold or a shift to a second orientation of the patient is detected. When a shift in the patient is detected prior to the time-on value being above the time-on threshold, the motion detection system 10 preferably starts detecting the time-on value for the second orientation and compares it to the time-on threshold for the second orientation. The same time-on threshold may be used for each orientation for the patient, but may alternatively be adjusted to accommodate to different qualities of orientations for each patient. In a first example, the patient may have been in the second orientation for a second orientation time-on value prior to shifting to the first orientation. The patient then shifts back to the second orientation prior to the time-off value for the second orientation being greater than the time-off value for the second orientation. As a result, the motion detection system 10 will adjust the time-on threshold for the second orientation to be a shorter time period to prevent the patient from being in the second orientation for too long. In a second example, the patient may have certain orientations that are at higher risk for skin ulcers than others. For example, the patient's right side may have a higher risk for skin ulcers and thus the time-on threshold for the right side may be lower than other orientations and the time-off threshold for the right side may be higher than other orientations.

In a third variation, the step of determining the appropriate orientation of the patient uses input from the nurse as to what the correct orientation for the patient is for a period of time. Any shifting of orientation from the indicated correct orientation before a time-on threshold is passed may be flagged as a warning to the nurse for attention, wherein the time-on threshold corresponds to the period of time entered by the nurse. For example, the nurse inputs into the motion detection system 10 that the patient should be on his or her left side for a time-on of at least one hour. If the patient is detected as having shifted from his or her left side in less than one hour, the nurse is called to shift the patient back onto his or her left side.

In a fourth variation, the step of determining the appropriate orientation of the patient uses an input from the nurse as to a first orientation that the patient should not be in for a period of time. Any shifting of orientation of the patient into the first orientation before a time-off threshold is passed may be flagged as a warning to the nurse for attention, wherein the time-off threshold corresponds to the period of time entered by the nurse. For example, the nurse inputs into the motion detection system 10 that the patient should not be on his or her left side for a time-off of at least one hour. If the patient is detected as having shifted onto his left side in less than one hour, the nurse is called to shift the patient off of his or her left side.

Although the method for determining the need for nurse attention is preferably at least one of the above variations, the method may be of any suitable type or sequence. The method for determining the need for nurse attention may also be any suitable combination of the above variations.

Figure 9:
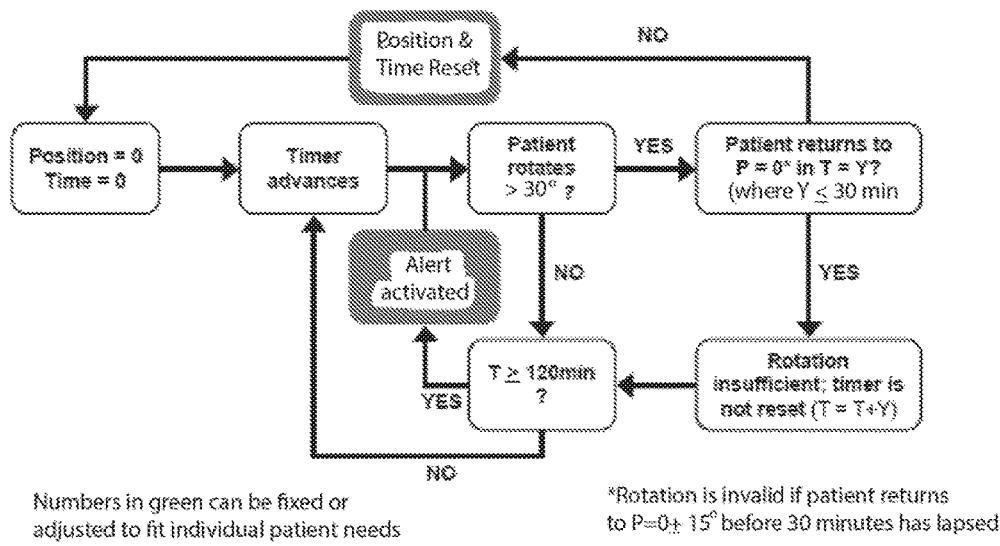
FIG. 9 illustrates a representative use case based on spatial (position) and temporal (time) information in a representative embodiment.
Figure 10:
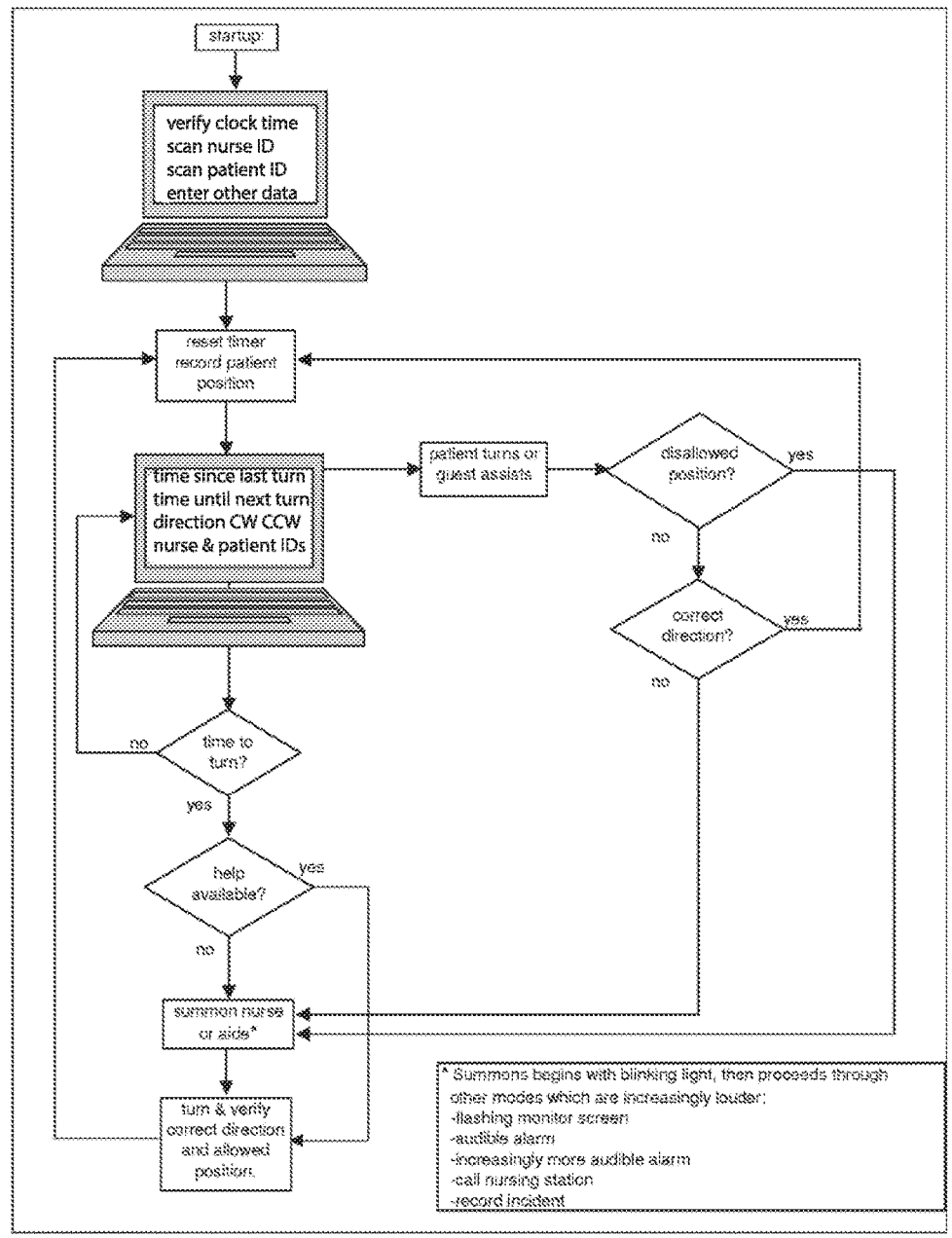
FIG. 10 illustrates a further example of a use case.

One skilled in the art will appreciate that the determination of whether to indicate an alert may depend on various programmable factors. A representative, but non-limiting, workflow for an alert might be as shown in FIG. 9, although many suitable variations may be implemented by programming or configuring different variables. FIG. 10 illustrates a representative process flow for the system operation in the patient turn monitoring and alert embodiment. The protocol for a representative "use" case might then proceed as follows.

Confirm that the bedside computer is plugged into power and network and turned on. A standard template of hospital personnel authorized to access the orders/protocol fields is displayed—the charge nurse indicates the name/position/title of authorized personnel. The template will display who can authorize and execute repositioning. Nurse ID badge barcode is scanned to identify the individual nurse and to allow entering of data into the bedside unit. Patient wristband ID barcode is scanned in order to identify the patient. Information can also be entered manually. Sensor barcode is scanned to identify the individual unique sensor. Room and bed number is entered into the bedside unit using touch screen. Repositioning protocol is entered into the bedside unit using the touch screen. Sensor is turned on, initialized and placed on the patient. Baseline position of sensor is established according to care needs. Confirmation of link is displayed on the touch screen. The nurse presses end of event command.

When nursing station alarm is activated and repositioning instructions are given, nurse goes to patient room and bedside. The nurse arrives and scans her badge barcode; preferably, this is required in order to make changes, as preferably the patient or other occupants of the room are prevented from making changes. Touch screen displays or voice instructs current repositioning order. The nurse then turns the patient. After a specified period of time the bedside unit confirms the turn. The nurse presses the end of event command.

The following describes further information regarding a reference implementation for the patient monitoring system for use with patients to avoid pressure ulcers. In this embodiment, a physically wearable, disposable sensor monitors the patient's position and transmits this information, e.g., by means of a radio signal, to a programmable bedside computer/receiver. The sensor is comfortable to wear, easy to apply and remove, rugged enough to remain in place and fully functional after showers, rolling over, etc., preferably activated by a power switch that remains water tight, and wherein an ON condition is indicated by an LED that is easily visible. The sensor continuously sends patient position to the bedside computer. Preferably, the bedside computer includes an easily viewable keyboard. In one embodiment, input of the initial patient position is provided to the bedside computer. The system reads and stores identity of the patient and perhaps the nurse on duty, e.g., by means of a bar code reader. The system also stores positions which, for a particular patient, are not acceptable. The system alerts the patient and/or medical personnel of the need to turn the patient (e.g., in 90° increments) every few hours, or other preset interval, in order to prevent pressure ulcers. In a preferred embodiment, the bedside computer maintains a continuous log of patient position and turning times and displays current position, time since last turn, time until next turn, direction and disallowed position(s) as well as patient and nurse identification. The bedside computer sounds an alert when the time to turn has been reached. A need-to-turn alert sequence preferably is capable of waking sleeping patients and/or alerting the nursing team. It may comprise a flashing light, a flashing computer screen, a low level audible alert, progressively louder audible alarms, and automatic telephone call to nursing station or nurse's pager. Preferably, the system sounds a different alarm if the patient is turned, or turns himself/herself, to a disallowed position. Visitors or other personnel in the room may turn the patient (depending on the nature and severity of the illness) thus relieving the nursing staff of the need to do so at each interval.

Figure 11:
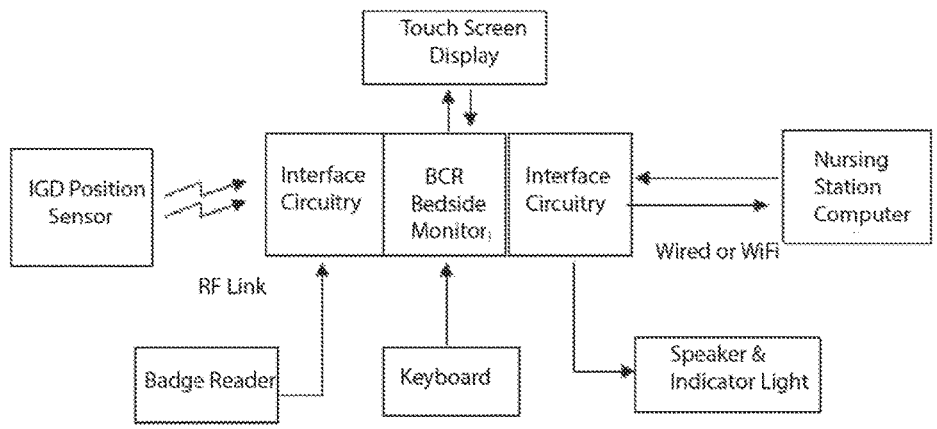
FIG. 11 illustrates a representative system using a handheld device as the bedside monitor.

In this above-described reference implementation, the sensor may be based on a wireless sensor device, such as the Freescale ZSTAR sensor (e.g., Model No. RD3152MMA7260Q), and the bedside computer may be a known device, such as an iPhone® or Android™ device, an iPad™, or any other mobile, tablet, laptop or the like, that includes an application, utility or other software to implement the above-described functionality and interfaces. In a preferred implementation, one or more of the above-described components of the system may be implemented as iPhone or other the like applications. A suitable receiver device at the nurse's station may be a USB compatible receiver, such as the Freescale ZSTAR MC13191, together with a programmed computer. FIG. 11 illustrates a possible reference.

The above-described techniques may be implemented outside of a medical or nursing facility, such as in a patient's (or, more generally, a user's) home. As noted above, the receiver may be implemented as an application in a device such as the iPhone. The application is s installed onto the phone and the user goes though a setup process (setting which sides are permissible, the length of time between turns, how the alerts are patterned, an automatic phone number that should be called if the patient has not turned, a URL that the unit may need to access (if the phone's web browser is used to access a server), patient identification data, permissible caregivers identification, and the like. The caregiver then attaches to the patient one or more "holder" bandages, e.g., at position(s) instructed by a physician, nurse or nurse practitioner. The holder receives a sensor unit (such as described above) and that has been charged. This approach reduces sterilization concerns. The sensor is turned on and is placed in the pocket on the upper surface of the bandage which is already attached to the patient. It is assumed that the bandages would be changed frequently, perhaps as often as the sensors are exchanged for charging. In one variant, the bandage contains a small magnet s integrated into the bandage, which, when in proximity to the sensor, turned the sensor on. This model has the attractive feature that the battery is only used when the sensor is in a bandage. The bandage is the on/off switch. Another variant is to use a separate antenna and reusable sensor. For example the bandage itself contains the antenna and the sensor "speaks" to the bandage, which then transmits to the phone via its antenna. Another alternative is to use known RFID tags and sensors. In the home care embodiment, the "local" devices may be connected to one or more remote monitoring and alert systems to facilitate the care protocol.

The disclosed subject matter provides numerous advantages. Every year, untold amounts of unnecessary suffering are endured and medical resources spent on care for pressure ulcers, an injury that could be prevented. This above-described monitoring system and method tracks the patient's position over time and ensures that proper turning is done within the time prescribed. At present, there are no products available which continuously monitor patient position and alert medical or other personnel of the need for turning.

The disclosed subject matter (or components of the system) may be implemented with any known or later-developed wireless and computer networking technologies. Thus, for example, the wireless infrastructure illustrated above may include any wireless client device, e.g., a cell phone, pager, a personal digital assistant (PDA, e.g., with GPRS NIC), a mobile computer with a smart phone client, or the like. A typical mobile device is a wireless access protocol (WAP)-enabled device that is capable of sending and receiving data in a wireless manner using the wireless application protocol. The wireless application protocol ("WAP") allows users to access information via wireless devices, such as mobile phones, pagers, two-way radios, communicators, and the like. WAP supports wireless networks, including CDPD, CDMA, GSM, PDC, PHS, TDMA, FLEX, ReFLEX, iDEN, TETRA, DECT, DataTAC, and Mobitex, and it operates with many handheld device operating systems, such as PalmOS, EPOC, Windows CE, FLEXOS, OS/9, and JavaOS. Typically, WAP enabled devices use graphical displays and can access the Internet (or other communication network) on so-called mini- or micro-browsers, which are web browsers with small file sizes that can accommodate the reduced memory constraints of handheld devices and the low-bandwidth constraints of a wireless networks. In addition to a conventional voice communication, a given mobile device can communicate with another such device via many different types of message transfer techniques including SMS (short message service), enhanced SMS (EMS), multi-media message (MMS), e-mail WAP, paging, or other known or later-developed wireless formats.

The patient device described herein may be implemented using any known or later developed RFID technologies. Such technologies are well-known and may be used for the patient wearable device and associated readers. As is well-known, radio frequency identification (RFID) is an automatic identification method that relies on storing and remotely retrieving data using devices called RFID tags or transponders. As used herein, an RFID tag is an object that can be attached to or incorporated into a product or person for the purpose of identification using radio waves. The RFID tags may be active (internally powered) or passive (powered by the received RF energy). Any commercial RFID tags and RFID systems for workflow and inventory management may be used for this purpose.

The other components illustrated comprise a set of one or more computing-related entities (systems, machines, process programs, libraries, functions or the like) that together facilitate or provide the inventive functionality described. In a typical implementation, the infrastructure comprises a set of one or more computers. A representative machine is a network-based server running commodity (e.g. Pentium-class) hardware, an operating system (e.g., Linux, Windows, OS-X, or the like), an application runtime environment (e.g., Java, .ASP) and a set of applications or processes (e.g., Java applets or servlets, linkable libraries, native code, or the like, depending on platform), that provide the functionality of a given system or subsystem. The service may be implemented in a standalone server, or across a distributed set of machines. Typically, a server connects to the publicly-routable Internet, a corporate intranet, a private network, or any combination thereof, depending on the desired implementation environment. Of course, any other hardware, software, systems, devices and the like may be used. More generally, the present invention may be implemented with any collection of autonomous computers (together with their associated software, systems, protocols and techniques) linked by a network or networks. As previously noted, the hardware and software systems in which the invention is illustrated are merely representative. The invention may be practiced, typically in software, on one or more machines. Generalizing, a machine typically comprises commodity hardware and software, storage (e.g., disks, disk arrays, and the like) and memory (RAM, ROM, and the like).

The particular machines used in the network are not a limitation of the disclosed subject matter. A given machine includes network interfaces and software to connect the machine to a network in the usual manner. While given components of the system have been described separately, one of ordinary skill will appreciate that some of the functions may be combined or shared in given instructions, program sequences, code portions, and the like.

Communications between the various devices and stations described above preferably are secured using known technologies.

While the above describes a particular order of operations performed by certain embodiments, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

Having described our invention, what we now claim is as follows.

The invention claimed is:

1. A method for monitoring an orientation of a person with respect to a defined turning protocol for the person, the method comprising:

receiving, via an input device, user input defining a person-specific restricted orientation associated with an injury at a specific side or area of the person's body, the person-specific restricted orientation comprising an orientation in which a patient support surface imparts pressure on the injured side or area of the person's body, sensing, with a sensor device configured to be physically wearable by the person, information representative of a physical orientation of the person, executing, by a processor, computer instructions stored in non-transitory computer-readable media to:

determine, based on the sensed physical orientation of the person, a turn of or by the person from a first orientation to a second orientation, determine both:

(a) whether the second orientation to which the person has turned is the restricted orientation defined for the person via the input device, and (b) whether the second orientation to which the person has turned is compliant with the defined turning protocol for the person, initiate an audible or visual alert in response to each one of the following:

a determination that the second orientation to which the person has turned is the restricted orientation, a determination that the second orientation to which the person has turned is non-compliant with the defined turning protocol, and a determination that a time spent in the second orientation exceeds a threshold time specified by the defined turning protocol, and adjust a timer of the defined turning protocol without initiating an audible or visual alert in response to a determination that the second orientation to which the person has turned (a) is compliant with the defined turning protocol and (b) is not the restricted orientation, and is thus a compliant turn.

2. The method of claim 1 wherein the input defining a person-specific restricted orientation for the person comprises input defining a side of the person's body with the injury.

3. The method of claim 1, wherein the input device is provided at a computer distinct from the wearable sensor device and communicatively coupled to the wearable sensor device by a wireless link.

4. The method of claim 1, wherein the input device comprises a keyboard.

5. The method of claim 1, further comprising, in addition to the processor initiating the audible or visual alerts, the processor causing a visual display of both (a) an indication of a current orientation of the person and (b) an indication of the user-defined restricted orientation associated with the injury at the specific side or area of the person's body.

6. The method of claim 1, further comprising, in addition to the processor initiating the audible or visual alerts, the processor causing a display of an indication of a current orientation of the person.

7. The method of claim 1, further comprising determining, and displaying an indication of, at least one of:

(a) an amount of time since a previously detected change in orientation of the person, or (b) an amount of time until an upcoming change in orientation of the person as defined by the defined turning protocol for the person.

8. The method of claim 1, wherein the audible or visual alert initiated in response to the determination that the time spent in the second orientation exceeds the threshold time specified by the defined turning protocol is different than the audible or visual alert initiated in response to the determination that the second orientation to which the person has turned is the restricted orientation.

9. The method of claim 1, wherein the sensor device comprises at least one accelerometer to generate information representative of the physical orientation of the person.

10. The method of claim 1, further comprising displaying an indication of a current orientation of the person.

11. A system for monitoring an orientation of a person, the system comprising:
an input device configured to receive user input defining a restricted orientation associated with an injury at a specific side or area of the person's body, the person-specific restricted orientation comprising an orientation in which a patient support surface imparts pressure on the injured side or area of the person's body,
a sensor device configured to be physically wearable by the person and configured to output orientation information representative of changes in the orientation of the person with respect to the physical support surface,
computer instructions stored in non-transitory computer-readable media,
an audio or visual output device, and
a processor in communication with the sensor device and the audio or visual output device, the processor configured to:
receive the orientation information output by the sensor device, and
execute the computer instructions to:
determine, based on the received orientation information, a particular turn of the person from a first orientation to a second orientation,
determine whether the second orientation to which the person has turned is the user-defined restricted orientation for the person defined by the received user input,
determine whether the second orientation is a correct orientation for the person according to a defined turning protocol for the person,
determine whether the particular turn from the first orientation to the second orientation is a compliant turn or a non-compliant turn based at least on (a) the determination of whether the second orientation is the user-defined restricted orientation for the person and (b) the determination of whether the second orientation is a correct orientation for the person according to the defined turning protocol for the person, and
based on the determination of whether the particular turn is a compliant turn or a non-compliant turn:
initiate an audible or visual non-compliant turn notification via the audio or visual output device if the particular turn is determined to be a non-compliant turn, and
not initiate an audible or visual notification via the audio or visual output device if the particular turn is determined to be a compliant turn.

12. The system of claim 11 wherein the input defining a restricted orientation for the person comprises user input defining a side of the person's body with the injury.

13. The system of claim 11, wherein the input device is provided at a computer distinct from the wearable sensor device and communicatively coupled to the wearable sensor device by a wireless link.

14. The system of claim 11, wherein the input device comprises a keyboard.

15. The system of claim 11, comprising a display device configured to visually display both (a) an indication of a current orientation of the person and (b) an indication of the user-defined restricted orientation associated with the injury at the specific side or area of the person's body.

16. The system of claim 11, wherein the sensor device comprises at least one accelerometer to generate information representative of the physical orientation of the person.

* * * * *